US008453508B2

(12) United States Patent
Delgado et al.

(10) Patent No.: US 8,453,508 B2
(45) Date of Patent: *Jun. 4, 2013

(54) TESTING OF SWING TYPE CHECK VALVES USING PHASED ARRAY SEQUENCE SCANNING

(75) Inventors: Jesse R. Delgado, San Antonio, TX (US); Hector Diaz, San Antonio, TX (US)

(73) Assignee: IHI Southwest Technologies, Inc., San Antonio, TX (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/965,575

(22) Filed: Dec. 10, 2010

(65) Prior Publication Data

US 2012/0144919 A1   Jun. 14, 2012

(51) Int. Cl.
*G01N 29/04* (2006.01)
(52) U.S. Cl.
USPC .................................. 73/618; 73/620; 73/625
(58) Field of Classification Search
USPC ................. 73/592, 596, 597, 553, 554, 599, 73/602, 609, 661, 644, 642, 618–620, 622, 73/624–625, 627–630
See application file for complete search history.

(56) References Cited

U.S. PATENT DOCUMENTS

| | | | | |
|---|---|---|---|---|
| 4,143,554 A | * | 3/1979 | Nagy et al. | 73/641 |
| 4,782,702 A | * | 11/1988 | Boone et al. | 73/597 |
| 4,920,802 A | * | 5/1990 | McMullin et al. | 73/597 |
| 4,977,778 A | | 12/1990 | Nafziger et al. | |
| 5,008,841 A | * | 4/1991 | McElroy | 702/39 |
| 5,154,080 A | * | 10/1992 | Hill et al. | 73/597 |
| 5,155,672 A | * | 10/1992 | Brown | 363/43 |
| 5,159,835 A | * | 11/1992 | Nafziger et al. | 73/584 |
| 5,228,342 A | | 7/1993 | McShane | |
| 5,236,011 A | | 8/1993 | Casada et al. | |
| 5,257,545 A | | 11/1993 | Au-Yang | |
| 5,392,652 A | | 2/1995 | Levesque et al. | |
| 5,471,138 A | | 11/1995 | Glass, III et al. | |
| 5,475,613 A | | 12/1995 | Itoga et al. | |
| 5,504,426 A | | 4/1996 | Ricci et al. | |
| 5,523,682 A | | 6/1996 | Leon | |
| 6,332,011 B1 | | 12/2001 | Johnson | |
| 6,637,267 B2 | * | 10/2003 | Fiebelkorn et al. | 73/587 |
| 6,865,243 B2 | | 3/2005 | Paillaman et al. | |
| 6,917,196 B2 | | 7/2005 | Kwun et al. | |
| 6,938,457 B2 | | 9/2005 | Johnson et al. | |
| 6,965,834 B2 | | 11/2005 | Saito et al. | |
| 7,412,890 B1 | | 8/2008 | Johnson et al. | |
| 7,503,227 B2 | | 3/2009 | Davis et al. | |
| 7,694,569 B2 | | 4/2010 | McGrath et al. | |
| 7,728,967 B2 | | 6/2010 | Ochiai et al. | |

(Continued)

*Primary Examiner* — Helen C. Kwok
(74) *Attorney, Agent, or Firm* — Gunn, Lee & Cave, P.C.

(57) ABSTRACT

A computer with a proper program generates a phased array sequence of signals. In a pulser with delays, the signals are fed through a multiplexor into a water wedge that is attached to a valve being tested. For a sequential operation of the valves from the open to the closed position, ultrasonic signals are transmitted through the fluid contained in the valve and reflected back through piezo-electric crystals to the multiplexor. By summation and merger of the signals, an image can be developed of the operation of the valve to determine if the valve is operating properly. By use of the water wedge, the top plate of the valve appears to disappear because the water wedge has the same refractive angle as the fluid contained in the valve.

12 Claims, 4 Drawing Sheets

U.S. PATENT DOCUMENTS

| | | |
|---|---|---|
| 7,784,347 B2 | 8/2010 | Messer et al. |
| 8,166,823 B2 * | 5/2012 | Lam et al. ................. 73/622 |
| 2003/0233880 A1 | 12/2003 | Siverling et al. |
| 2009/0045994 A1 | 2/2009 | Drummy et al. |
| 2009/0293621 A1 | 12/2009 | Kitazawa et al. |
| 2010/0018311 A1 | 1/2010 | Batzinger et al. |
| 2010/0071470 A1 | 3/2010 | Junker et al. |
| 2010/0170344 A1 | 7/2010 | Lesage et al. |
| 2010/0218609 A1 | 9/2010 | Reed et al. |
| 2012/0180570 A1 * | 7/2012 | Delgado et al. ................. 73/592 |

* cited by examiner

TESTING OF SWING TYPE CHECK VALVES USING PHASED ARRAY SEQUENCE SCANNING

BACKGROUND OF THE INVENTION

1. Technical Field

This invention relates to the non-intrusive testing of valves and, more particularly, to the testing of swing-type check valves using phased array sequence scanning.

2. Brief Description of the Prior Art

In the past, if someone wanted to see if a valve was operating properly flow through the valve was the first thing checked. If more information was desired, the valve could be taken apart. As technology advanced, other ways of checking the internal operation of the valve was developed. For example, a magnetic field may be used to determine the position of the disc in a check valve as is shown in U.S. Pat. No. 5,236,011. Also, ultrasonic vibrations have been used to monitor check valves to determine if they are operating properly. Even a combination of acoustic and magnetic techniques have been used in the past to monitor the operation of valves (see U.S. Pat. No. 5,008,841).

In the past, many different techniques of using ultrasonics have been developed to determine either the condition or the position of a valve without taking the valve apart. However, these non-intrusive inspection techniques normally did not give all of the information necessary to determine if a valve is operating properly. For example, the hinge pin on which the clapper of a check valve operates may be worn over a period of time. If this condition is not detected before the hinge pin breaks, a catastrophic failure would result. Typical non-intrusive inspection techniques are not able to detect wear on the hinge pin of a disc-type check valve.

In the last few years, the use of phased arrays to generate a wave front of ultrasonic signals has been used in different types of inspection techniques. For example, phased array has been used to measure flow of a fluid through a pipe as is shown in U.S. Pat. No. 7,503,227. Also variable angle ultrasonic transducers have been used in inspection techniques for pipes, conduit, plates or other foreign metallic members that may have irregularities in the surface of the test member (see U.S. Pat. No. 5,392,652).

As the capability of computers has increased dramatically in recent years, the use of a phased array ultrasonic signal has also been used in the testing of various equipment (see U.S. Patent Publication No. US 2009/0045994 A1). The use of phased array for three-dimensional ultrasonic inspection has also begun to be used in the industry (see U.S. Patent Publication No. US 2009/0293621 A1 and U.S. Pat. No. 7,784,347). Even combinations of laser beams and ultrasonic signals have been used in maintenance programs for testing equipment (see U.S. Pat. No. 7,728,967). Ultrasonic phased array has been used for some time in the testing of weld joints and pipes (U.S. Pat. No. 7,412,890).

As the nuclear regulatory industry has developed, a need has also developed for a very reliable method for non-intrusive inspection of the valves in a nuclear power plant. The operators needs to know with certainty that the valves are operating properly. Also, the operators need to know if a valve has begun to wear to the point where the valve should be serviced or repaired. This cannot be done with the inspection techniques that have been developed and used in the past.

BRIEF SUMMARY OF THE INVENTION

It is an object of the present invention to provide a non-intrusive inspection technique for valves.

It is another object of the present invention to provide for testing of swing-type check valves using phased array sequence scanning.

It is another object of the present invention to use a non-intrusive technique of phased array sequence scanning to determine if a valve is operating properly.

It is yet another object of the present invention to provide the use of phased array sequence scanning in a non-intrusive technique to test the proper operation of a valve.

It is yet another object of the present invention to provide a water wedge in combination with phased array sequence scanning to test the proper operation of a swing-type check valve by use of a non-intrusive technique.

It is another object of the present invention to use a water wedge to transmit a phased array sequence scanning to a valve full of fluid to test proper operation of the valve.

A user setup is provided that consists of a computer properly programmed to create a phased array. The phased array is fed through a pulser with delays to a multiplexor. The multiplexor receives the signals from the pulser and creates a serial set of phased array signals, which phased array signals are sent to a plurality of piezo-electric crystals mounted on a water wedge. A water wedge is a wedge-like structure made from a plastic mixture that has the same refraction index as water.

The water wedge is mounted on a steel plate forming the top of a check valve. If the check valve is full of liquid, phased array sequence scanning can be used to monitor the operation of the check valve by receiving reflected signals back through the water wedge via receiving piezo-electric crystals, which receiving piezo-electric crystals provide serial input into the multiplexor. The output of the multiplexor sends parallel signals to a receiver with delays, which received signals are summed in a summation device. The summed signals feeds through a phase array acquisition and control to an image development and display. In the image development and display, the operation of the check valve can be monitored to determine if it is operating properly, or if repairs are necessary.

BRIEF DESCRIPTION OF THE DRAWINGS

The patent or patent application file contains at least one drawing executed in color. Copies of this patent or patent application publication with color drawings(s) will be provided by the Office upon request and payment of the necessary fee.

DESCRIPTION OF THE PREFERRED EMBODIMENT

Figure 1:
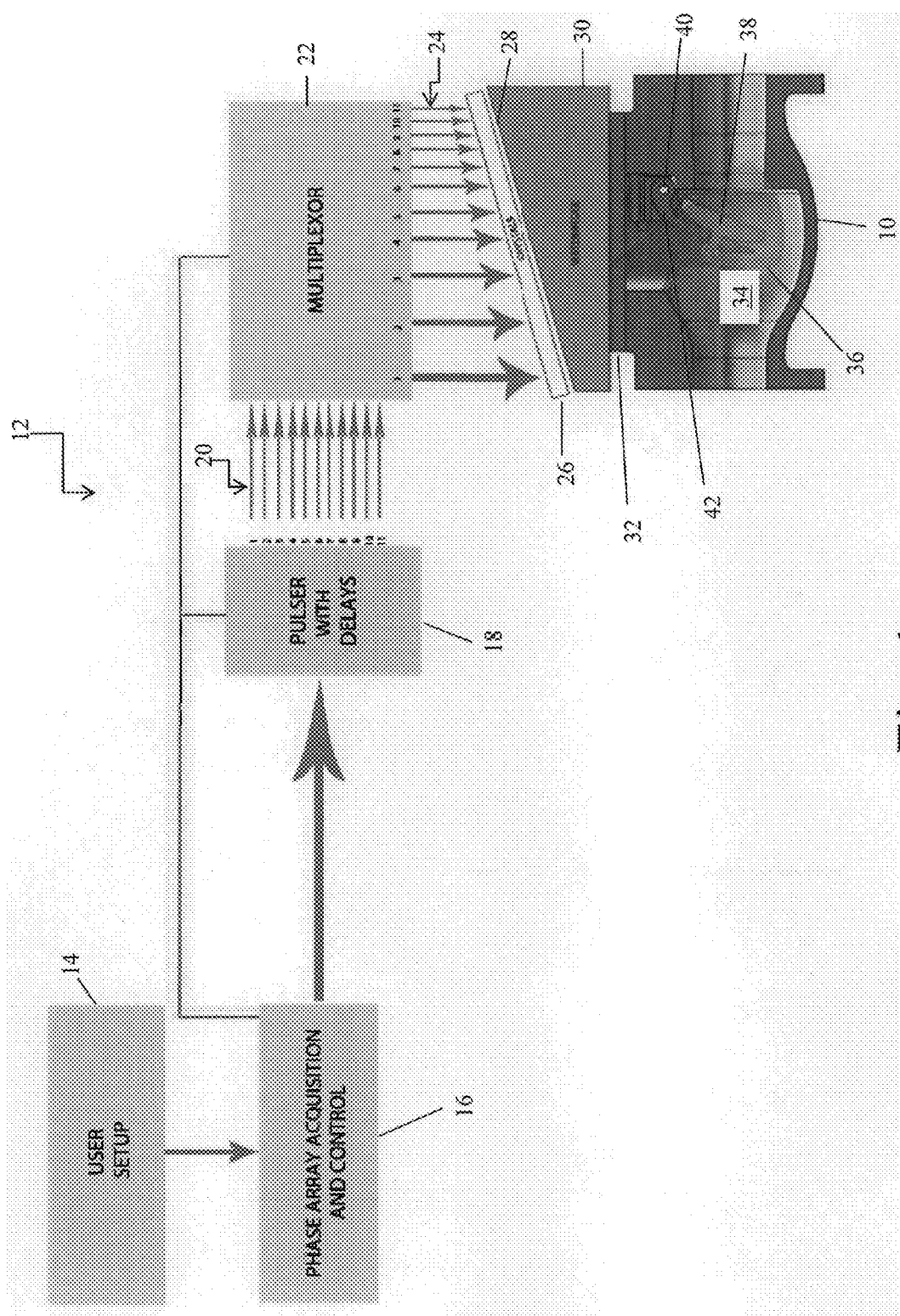
FIG. 1 is a combined pictorial and block diagram illustrating the use of phased array sequence scanning to generate phased array signals in a swing-type check valve.

Referring now to FIG. 1, a swing-type check valve 10 is being tested by phased array sequence scanner illustrated generally by the reference numeral 12. The phased array sequence scanner 12 has a user setup 14 that will include a computer that is programmed to generate a wave front to be used in testing the swing-type check valve 10. If some other type of valve is being tested, the user setup 14 can be varied and the program changed to generate the particular type of wave front desired for the valve under test.

The wave signal from the user setup 14 feeds to a phased array acquisition and control 16. The phased array acquisition and control 16 takes the instructions from the software contained in the user setup 14 and fires the voltages in a timing sequence as determined by the computer program. The signals from the phased array acquisition and control 16 feed through a pulser with delays to generate spike signal voltages 20 that are fed through multiplexor 22. In the illustration as shown in FIG. 1, a total of eleven voltage spike signals 20 are generated, but this number can vary depending upon design of the phased array sequence scanner 12.

The multiplexor 22 manages the outgoing pulses 24 which fires transmit piezo-electric crystals 26. In the present embodiment, because there are eleven spike voltage signals 20 being received from the pulser with delays 18, there will be eleven transmit piezo-electric crystals 26. In this preferred embodiment, the number of piezo-electric crystals 26 is eleven. However, the number of piezo-electric crystals can vary according to the preference of the end user.

The number of piezo-electric crystals could be as few as three, but the upper end is controlled only by the number of discreet signals that can be transmitted and received. Twenty or thirty piezo-electric crystals could be used almost the same as eleven are being used in this preferred embodiment. The piezo-electric crystals can be naturally occurring such as quartz, but man-made lattices that form a piezo-electric crystal are better because of the quality control.

The transmit piezo-electric crystals 26 are attached to the inclined angle 28 of water wedge 30. The inclined angle 28 can vary from 0° to 70°, but Applicant has found approximately 20° to be ideal. Water wedge 30 is not actually made from water, but is made from a plastic mixture that has the same refraction index as water. Also, the water wedge 30 as illustrated in FIG. 1, is not to scale, but is illustrated in a manner that is approximately ten times its actual size when compared to the swing-type check valve 10 located there below. The water wedge 30 is enlarged for illustration purposes only.

During a normal test, the swing-type check valve 10 will be full of liquid. Because the water wedge 30 has the same refraction index as water, during a test, it will appear as if the top plate 32 of a check valve 10 is not present. This gives a much better signal. Therefore, the water wedge 30 is specifically designed to have approximately the same refraction index as the fluid contained inside of swing-type check valve 10.

In normal operation, the user setup 14 with the computer and program contained therein will cause the phased array acquisition and control 16 to generate signals that fed to the pulse with delays 18 that creates timed spike voltage signals 20 that feed through multiplexor 22. From multiplexor 22, the outgoing pulse signals 24 fire the transmit piezo-electric crystals 26 which generate a wave front in water wedge 30. The wave front flows through top plate 32 and into the chamber 34 of swing-type check valve 10. The wave front 36 is illustrated by the pie-shaped shaded area within chamber 34. The wave front 36 encompasses the disc 38 suspended from pin 40 through the disc arm 42. The wave front 36 will be sequenced over time to follow an entire cycle of a disc 38 within swing-type check valve 10.

Figure 2:
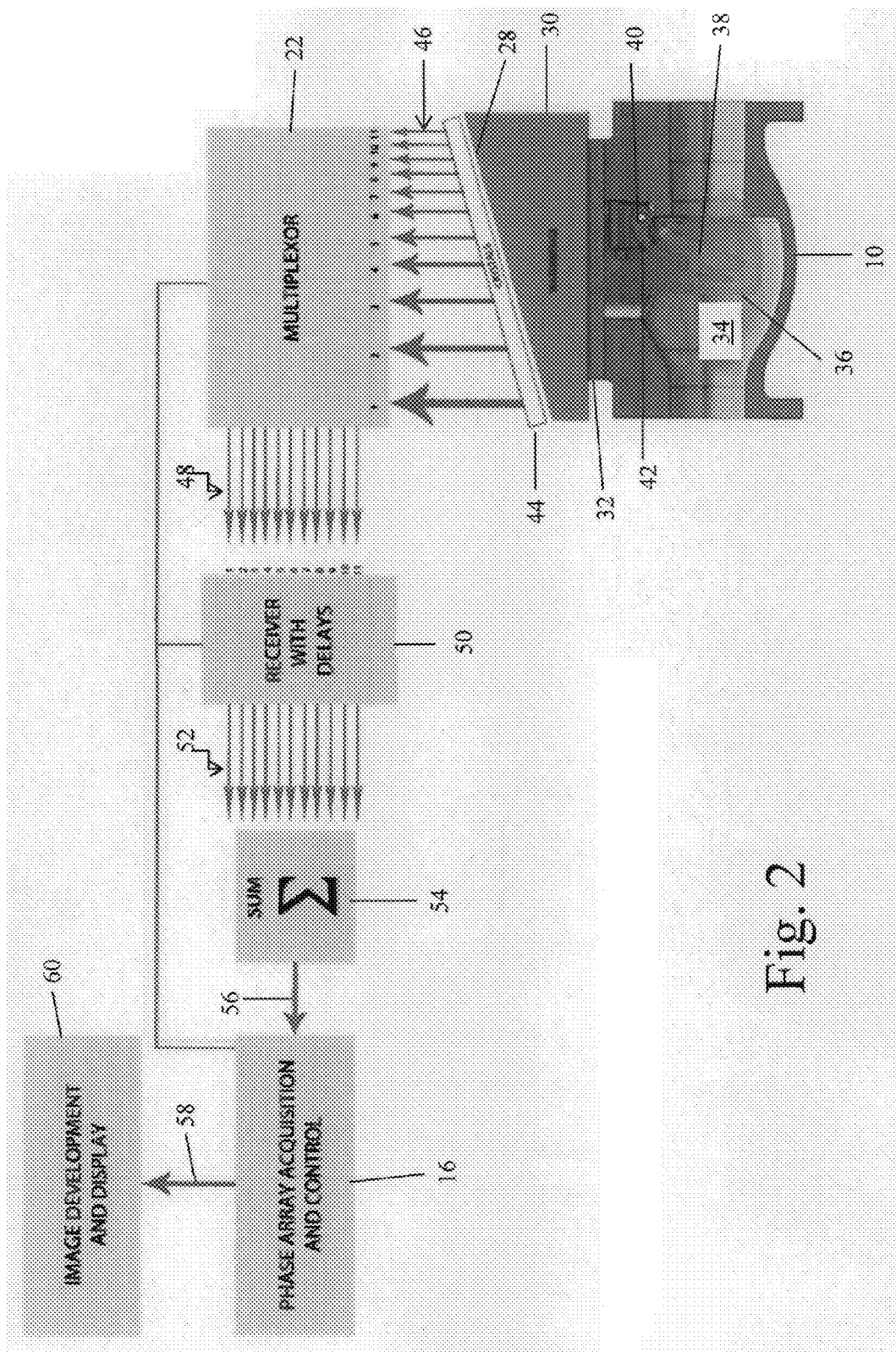
FIG. 2 is a combination pictorial and block diagram using phased array sequence scanning to illustrate the receiving of reflected signals resulting from the phased array sequence scanning.

Referring now to FIG. 2, in response to the wave front 36, acoustic signals will be received back through the top plate 32 and water wedge 30 to the receiving piezo-electric crystals 44. While the same piezo-electric crystal could be used to receive or transmit, in this preferred embodiment, the receiving piezo-electric crystals 44 are different from the transmitting piezo-electric crystals 26. The acoustic signals received via the receiving piezo-electric crystals 44 through water wedge 30 generate reflection signals 46. The reflection signals 46 are processed through multiplexor 22 to generate return parallel signals 48 that feed into receiver with delays 50. From the receiver with delays 50, reflected signals 52 feed into a summation device 54, which gives a summed output 56 to the phased array acquisition and control 16. The phased array acquisition and control 16 provides an image signal 58 to image development and display 60. The image development and display 60 gives a visual image of what is happening inside of swing-type check valve 10 through its normal operation if phased array sequence scanning is used.

The image development and display 60 uses a combination of signal amplitude and timing to form an image as to the operation of a swing-type check valve. Therefore, time of flight of a particular pulse inside of the swing-type check valve 10 is important as well as the amplitude of each signal.

Figure 3:
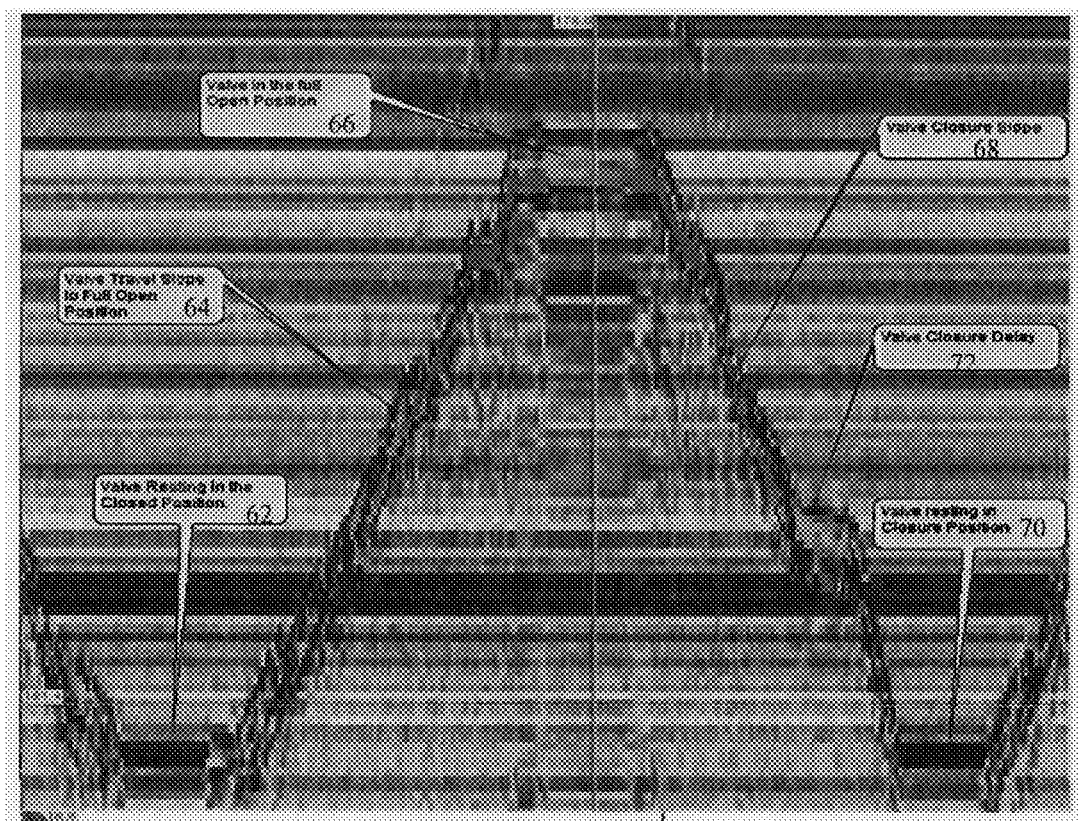
FIG. 3 is a color recording of final data results for an actual swing-type check valve using phased array sequence scanning.

Referring now to FIG. 3, the image being shown is the image that would be recorded over time during the actual operation of the check valve. If a swing-type check valve is operating properly, a valve closed signal 62 will be generated. As the disc on the valve opens, a valve opening signal 64 shows the travel of the disc when it goes from the closed position to the full open position. When the valve is full open, a valve open signal 66 is generated.

The main signal is associated with the color red. Red means there is a lot energy being returned at that point during the cycle.

During the reverse operation, a valve closing signal 68 is generated which is a downward slope as shown in FIG. 3. When the disc of the swing-type check valve closes, another valve closed signal 70 is generated. However, for the check valve being tested as illustrated in FIG. 3, there is a valve closure delay signal 72 between the valve open signal 66 and the valve closed signal 70. This valve closure delay signal 72 indicates a problem in the valve such as wear of pin 40 shown in previous FIGS. 1 and 2. The valve closure delay signal 72 indicates there is a problem with the valve under test which could be due to wear. Therefore, before a catastrophic failure occurs, the valve should be either repaired or replaced.

By looking at the phased array sequence scanning signal shown in FIG. 3, an operator can quickly tell if (1) the valve being tested is operating properly, (2) the valve being tested is worn or has some other defect and (3) the valve may cause problems in the near future. The signal shown in FIG. 3 is easily understood by the operator.

Figure 4:
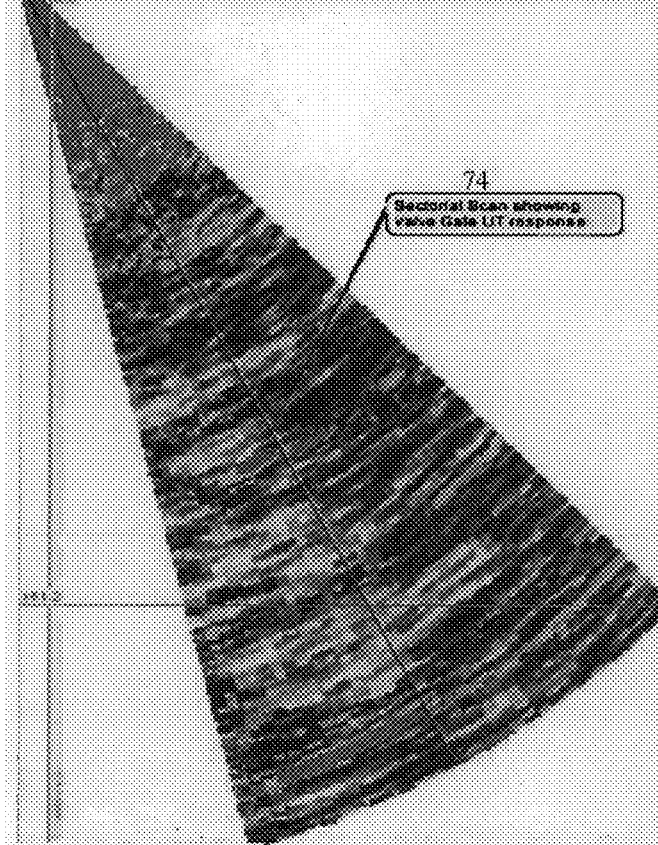
FIG. 4 is a cross-sectional view of the sound beam interacting with the disc of the check valve whose data is shown in FIG. 3.

Referring now to FIG. 4, the pie-shaped figure is actually a cross-sectional view of the sound beam interacting with the valve and valve disc as previously shown in FIG. 3. However, the cross-sectional view shown in FIG. 4 is harder to interpret than the wave form shown in FIG. 3. In FIG. 4, the two red dots 74 actually show the valve gate moving from the full open to the full closed position. It is much more difficult to get meaningful information out of the pie-shaped cross-sectional view shown in FIG. 4, but the image shown in FIG. 3 is easily understood by the operator.

Applicant has found that if the inclined angle 28 of the water wedge 30 is 15°, it provides the good data. The view as shown in FIG. 3 is a volume corrected sound beam at 15°. The sound energy can either be measured at (1) a single angle or (2) all the sound energy can be merged to form one picture. Each has their advantages and disadvantages.

Figure 5:
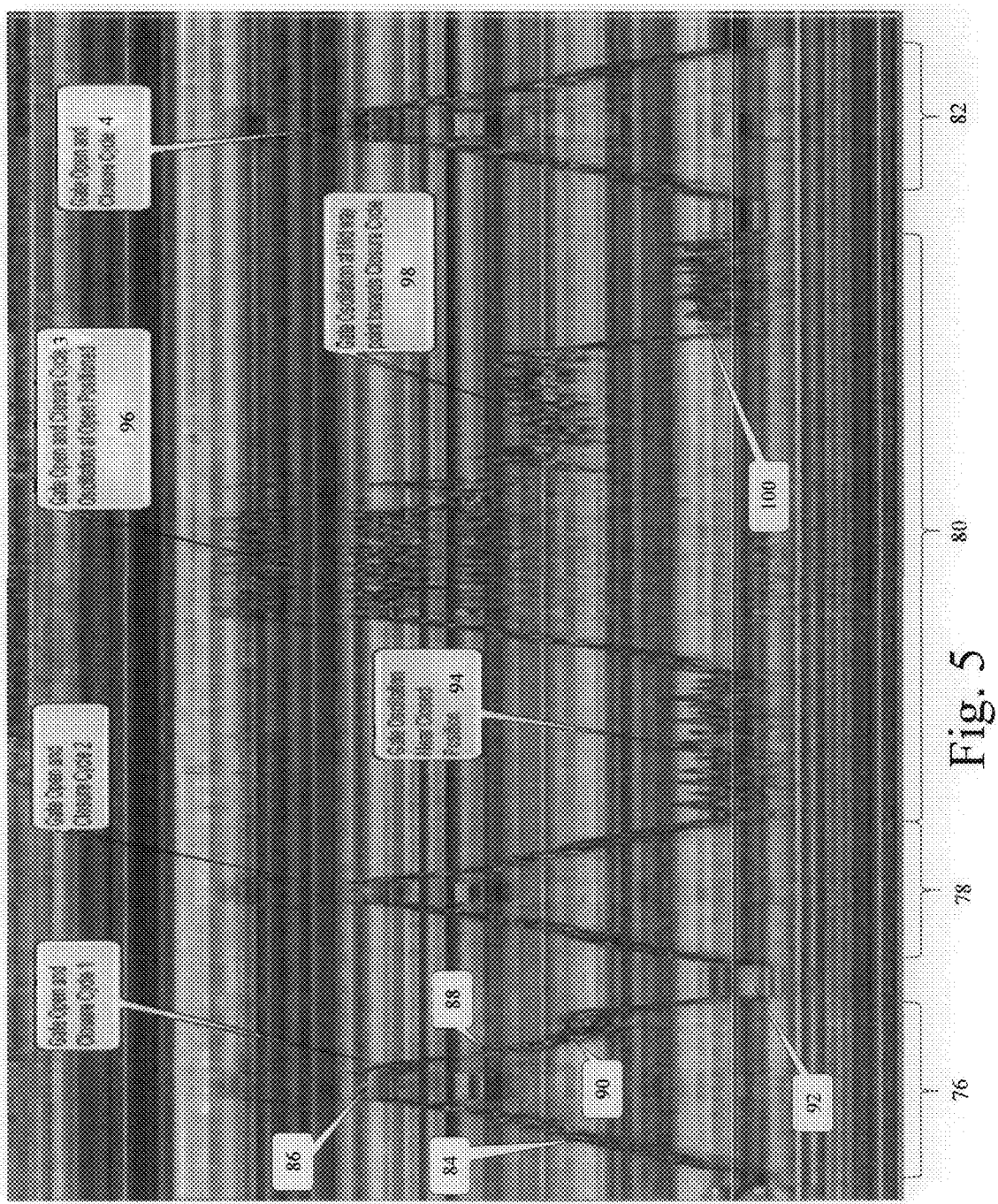
FIG. 5 is an analysis of four different check valves using phased array sequence scanning.

Referring to FIG. 5, the phased array sequence scanning of four different valves 76, 78, 80 and 82 are shown in cycles 1, 2, 3 and 4, respectively. Cycle one for valve 76 has a normal open cycle as is represented by the incline 84. The full open position 86 is also normal for valve 76. During the closing cycle 88, there is a valve closure delay 90 caused by wear inside of valve 76. The valve closure delay 90 is typical of wear in the pin 40 (see FIGS. 1 and 2) of a swing-type check valve. When fully closed, a closed signal 92 will again be given.

Cycle two is for a normally operating swing-type check valve 78 with no signs of undue wear or any other malfunctions.

However, valve 80, as is represented by gate open and closing cycle three has numerous problems. The gate or disc 38 in valve 80 has a tendency to oscillate near the closed position. The gate oscillation is illustrated by reference numeral 94. Also, when fully opened, the valve 80 again has oscillations at the open position as represented by the numeral 96. During the closure cycle of valve 80, there is gate oscillation at a midway position of the valve as represented by numeral 98. Again, when valve 80 is fully closed, there is again gate oscillations at the closed position as indicated by reference numeral 100. The valve 80 as shown in cycle three is about to have a catastrophic failure. During catastrophic failure any of a number of things could occur such as the disc coming off of the hinge pin or other types of similar failure. A valve operating similar to valve 80 should be replaced immediately.

Valve 82 as represented by cycle four is again a normal functioning valve.

As can be seen by looking at FIGS. 3 and 5, when phased array sequence scanning is used in testing swing-type check valves, the operator can easily see if the valve is functioning properly.

For the phased array sequence scanning to operate properly, the valve being tested should be full of liquid. If there is only liquid upstream of the disc, the valve can still be tested but the water wedge would have to be positioned upstream of the hinge point for the disc.

If it is desired to use the phased array sequence scanning on some other type of valve other than a hinged type check valve, a known signal will have to be generated for a good, properly operating valve. Thereafter, in checking similar type valves, future signals would be compared to the known signal to determine if the valve is operating properly.

We claim:

1. A method of testing operation of a valve filled with fluid to determine if the valve is operating properly, said method comprising the following steps:
   providing a user setup that includes programming a computer to generate a phased array of output signals;
   converting said phased array of output signals into phased outgoing pulses;
   feeding said phased outgoing pulses to transmitting piezo-electric devices attached to a water wedge mounted on said valve;
   generating from said phased outgoing pulses an acoustical phased wave front in said fluid;
   receiving reflected signals in said fluid by receiving piezo-electric devices attached to said water wedge;
   summing said reflected signals to give an output; and
   displaying said output to visually indicate condition of said valve during operation.

2. The method of testing operation of a valve filled with fluid to determine if the valve is operating properly as recited in claim 1 including after said converting step an additional step of first multiplexing said phased outgoing pulses in a multiplexor and after said receiving step an additional step of second multiplexing said reflected signals in said multiplexor.

3. The method of testing operation of a valve filled with fluid to determine if the valve is operating properly as recited in claim 2 wherein said water wedge is a wedge-shaped solid material with a refraction index approximately the same as water.

4. The method of testing operation of a valve filled with fluid to determine if the valve is operating properly as recited in claim 3 wherein said water wedge is attached to a top plate of said valve, an angle of said water wedge with respect to said top plate being between 0° to 70°.

5. The method of testing operation of a valve filled with fluid to determine if the valve is operating properly as recited in claim 4 wherein said valve is a swing type check valve with a disc.

6. A method of testing in situ a swing type check valve filled with fluid to determine if the valve is operating properly, said method comprising:
   mounting a water wedge on a relatively flat surface of said swing type check valve;
   setting up a computer with a program to generate phased signals;
   generating said phased signals;
   creating from said phased signals a series of pulsed signals with delays;
   first feeding said series of pulsed signals with delays through a multiplexor to transmit piezo-electric crystals;
   transmitting an array of acoustical waves through said water wedge and said relatively flat surface into said fluid, said array of acoustical waves being caused by said series of pulsed signal in said transmit piezo-electric crystals;
   receiving a reflected array of acoustical waves in receiving piezo-electric crystals through said relatively flat surface and said water wedge, said reflected array of acoustical waves causing reflection signals in said receiving piezo-electric crystals;
   second feeding said reflection signals through said multiplexor to a receiver with delay to generate a series of output signals;
   summing said series of output signals to give a summed output; and
   displaying said summed output over an operation cycle of said swing type check valve.

7. The method of testing in situ a swing type check valve filled with fluid to determine if the valve is operating properly as recited in claim 6 wherein said relative flat surface is a top of said swing type check valve.

8. The method of testing in situ a swing type check valve filled with fluid to determine if the valve is operating properly as recited in claim 7 wherein said water wedge is made from a plastic mixture with a refraction index being approximately the same as water.

9. The method of testing in situ a swing type check valve filled with fluid to determine if the valve is operating properly as recited in claim 8 wherein said testing is over at least one full cycle of said swing type check valve.

10. The method of testing in situ a swing type check valve filled with fluid to determine if the valve is operating properly as recited in claim 8 wherein said transmit piezo-electric crystals and said receiving piezo-electric crystals are mounted at an angle of said water wedge, said angle being relative to said top.

11. The method of testing in situ a swing type check valve filled with fluid to determine if the valve is operating properly as recited in claim 10 wherein said angle varies between 0° to 70°.

12. The method of testing in situ a swing type check valve filled with fluid to determine if the valve is operating properly as recited in claim 7 wherein an angle of said water wedge relative to said top is around 15° to 20°.

* * * * *